United States Patent
Lantz et al.

(10) Patent No.: US 6,339,178 B1
(45) Date of Patent: Jan. 15, 2002

(54) SYNTHESIS OF 1,1,1-TRIFLUOROETHANE BY FLUORINATION OF 1-CHLORO-1, 1-DIFLUOROETHANE

(75) Inventors: Andre Lantz; Sylvain Perdrieux, both of Vernaison; Dominique Garrait, Millery; Laurent Wendlinger, St-Genis-Laval, all of (FR)

(73) Assignee: Atofina, Puteaux (FR)

( * ) Notice: Subject to any disclaimer, the term of this patent is extended or adjusted under 35 U.S.C. 154(b) by 35 days.

(21) Appl. No.: 09/929,502

(22) Filed: Jun. 22, 2000

Related U.S. Application Data

(63) Continuation of application No. 08/895,365, filed on Jul. 16, 1997, now abandoned.

(30) Foreign Application Priority Data

Jul. 16, 1996 (FR) .............................. 96 08874

(51) Int. Cl.[7] .............................. C07C 17/00
(52) U.S. Cl. ...................... 570/167; 570/165; 570/166; 570/168; 570/169
(58) Field of Search ................ 570/167, 165, 570/166, 168, 169

(56) References Cited

U.S. PATENT DOCUMENTS 2,669,590 A    2/1954   Miller et al.
2,744,147 A    5/1956   Milks
2,744,148 A    5/1956   Ruh
3,456,025 A    7/1969   Gardner
5,569,793 A   10/1996   Bergougnan et al.

FOREIGN PATENT DOCUMENTS

| EP | 98341 | 1/1983 |
| EP | 421830 | 4/1991 |
| EP | 703204 | 3/1996 |
| EP | 712826 | 5/1996 |
| FR | 2365542 | 4/1978 |
| WO | 96/055156 | 2/1996 |

OTHER PUBLICATIONS

French Search Report dated Feb. 28, 1997.
Guo, et al., "Preparation of 1,1,1–trifluoroethane by liquid––phase fluorination of 1,1,1–dichlorofluoroethane", *Chemical Abstracts*, vol. 24, No. 19, May 1996, p. 1207, No. 260356.
W.B. Whalley, "Fluorination of organic compounds with anhydrous hydrogen fluoride. Part I., The preparation of fluoroform and certain derivatives", *Journal of the Society of Chemical Industry*, vol. 6, 1947, pp. 247–430, XP002026190.

*Primary Examiner*—Alan Siegel
(74) *Attorney, Agent, or Firm*—Smith, Gambrell & Russell, LLP

(57) ABSTRACT

The subject of the invention is the manufacture of 1,1,1-trifluoroethane by fluorination or 1-chloro-1,1-difluoroethane with anhydrous hydrofluoric acid. The reaction is carried out in the liquid phase and in the presence of a fluorination catalyst.

15 Claims, No Drawings

SYNTHESIS OF 1,1,1-TRIFLUOROETHANE BY FLUORINATION OF 1-CHLORO-1,1-DIFLUOROETHANE

This application is a continuation of application Ser. No. 08/895,365, filed Jul. 16, 1997 now abandoned.

The present invention relates to the field of fluorinated hydrocarbons and its subject is more particularly the manufacture of 1,1,1-trifluoroethane (known in the trade under the name F143a) by fluorination of 1-chloro-1,1-difluoroethane (F142b) with arhydrous hydrofluoric acid (HF).

Since chlorofluorocarbons (CFCs) were identified as one of the factors responsible for accelerating the deterioration in the stratospheric ozone layer, political and industrial players have been irrevocably committed to a process of substitution of CFCs. This substitution process relates to essential industrial sectors, such as the food refrigeration procedure, building insulation, air conditioning, microelectronics, and the like.

Searches to find replacements for these compounds were firstly focused on products containing hydrogen atoms (HCFCs) and then on products which no longer contain chlorine: hydrofluorocarbons (HFCs).

One of these HFC compounds, which does not contain chlorine and is thus without effect on the ozone layer, is 1,1,1-trifluoroethane (F143a). This compound is mainly intended, as a mixture with other HFCs, to replace F22 (chlorodifluoromethane) and F502 (azeotropic mixture of F22 and chloropentafluoroethane) in the field of refrigeration, air conditioning and other applications. There is thus great advantage in developing the simplest possible process for producing F143a.

Various processes for the preparation of F143a have been described in the literature. Thus, it is known to prepare F143a by fluorination of 1,1,1-trichloroethane, either in the gas phase (U.S. Pat. Nos. 2,744,148 and 2,744,147) or in the liquid phase. In the latter case, the fluorination is preferably carried out in the presence of a fluorination catalyst and Patent Application WO 96/5156 recommends in particular the fluorination of trichloroethane in the presence of pentavalent antimony halides.

The fluorination of vinylidene fluoride ($CF_2=CH_2$) has also been described, both in the gas phase (U.S. Pat. No. 2,669,590) and in the liquid phase (EP 703,204). This last process can be carried out in the absence of catalyst and would provide excellent results. However, on account of the high cost of vinylidene fluoride, such a process does not appear to be viable industrially; this is because vinylidene fluoride is obtained industrially by pyrolysis of 1-chloro-1, 1-difluoroethane (F142b) which is itself generally obtained by liquid phase fluorination of 1,1,1-trichloroethane or of vinylidene chloride in the absence or in the presence of catalyst (see, for example, Patents EP 98341, FR 2,365,542 and EP 421,830).

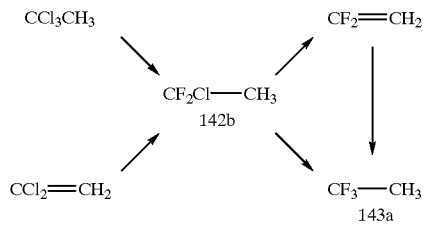

F142b is an important industrial product which is used as starting material in the manufacture of vinylidene fluoride ($VF_2$) but which, as HCFC, is also used as a replacement for certain CFCs, in particular as blowing agent in the foam industry and as propellent in the aerosol industry.

A process for the direct and economical manufacture of F143a from F142b is thus particularly advantageous. There exist in the literature only two publications relating to the fluorination of F142b to F143a (U.S. Pat. Nos. 3,456,025 and 2,767,227). These processes consist in carrying out the fluorination of F142b in the gas phase at high temperature in the presence of a fluorination catalyst. Although these two patents do not teach anything regarding the lifetime of the catalyst, it is known that the disadvantage of gas phase fluorination processes generally lies in a rapid deactivation of the catalyst.

It has now been found that, in the presence of a fluorination catalyst, F142b and anhydrous hydrofluoric acid react very rapidly in the liquid phase to form F143a very selectively.

The subject of the present invention is thus a process for the manufacture of F143a which is easy to implement industrially, characterized in that it comprises the fluorination of F142b with anhydrous hydrofluoric acid in the liquid phase in the presence of at least one fluorination catalyst.

The fluorination catalyst(s) which can be used in the process according to the invention are active catalysts which are well known for liquid phase fluorination reactions, such as halides, oxides and oxyhalides of elements belonging to groups IIIa, IVa and Va and to subgroups IVb, Vb and VIb. Use may more especially be made, among the elements selected from the columns of the Periodic Classification, of titanium, niobium, tantalum, molybdenum, boron, tin and antimony. Compounds containing antimony are particularly well suited. Halides are more particularly chosen as antimony derivatives; a typical example is antimony pentachloride $SbCl_5$ or the pentavalent antimony chlorofluorides formed in situ by partial fluorination of $SbCl_5$.

The amount of catalyst to be employed in this liquid phase fluorination can vary within wide limits. Expressed as a percentage by weight of metal, in particular of antimony, the catalyst content of the liquid reaction mixture is, however, generally between 0.01 and 10%, preferably between 0.1 and 5%.

The possibility of being able to use such small amounts of catalyst is entirely surprising because liquid phase fluorinations are generally carried out in the presence of large amounts of catalyst. Thus, in the process for the preparation of F143a by fluorination of 1,1,1-trichloroethane, as described in the abovementioned Patent Application WO 96/5156, the catalyst content of the reaction mixture is from 15 to 50%.

The pressure under which the process according to the invention is carried out is not critical in itself, from the moment that it enables the reaction to be carried out in the liquid phase, that is to say that it is sufficient to maintain the reactants present in the reactor essentially in the liquid form. It varies according to the temperature of the reaction mixture and according to the composition of this reaction mixture. The absolute pressure of the reaction system is generally chosen between 5 and 30 bar, preferably between 7 and 20 bar. The fluorination reaction of F142b to F143a releases hydrochloric acid. If it is desired to separate this HCl by distillation, it is advantageous to carry out the fluorination under a pressure which is sufficiently high to be able to condense the HCl under good conditions and, in this case, it is advantageous to operate at a pressure greater than approximately 11 bar. However, this is not essential and the HCl can be separated by any means other than a distillation, such as, for example, washing with water.

The process according to the invention can be carried out within a wide temperature range. Generally, the process is carried out at a temperature greater than 0° C. and less than 120° C. However, the temperature advantageously does not exceed 100° C. and the reaction is preferably carried out at a temperature of between 10 and 85° C. The use of such low temperatures, made possible by the very high reactivity of F142b, makes it possible to minimize the formation of by-products.

For the purpose of maintaining the activity of the catalyst, in particular that of antimony pentahalides, and of preventing deactivation by reduction to antimony trihalide, it may be advantageous to carry out the fluorination in the presence of a small amount of chlorine. The chlorine can be added periodically or continuously. The amount of chlorine supplied with the F142b is generally less than 2.5 mol of chlorine per 100 mol of F142b, preferably less than 1 molar %. The amount of chlorine can be very low, indeed zero, and it becomes lower as the temperature becomes lower. This is because it has been shown that, although it is difficult to make F142b react with chlorine, in the presence of $SbCl_5$ or of other Lewis acids, it nevertheless reacts to give, inter alia, chlorination products of the 130 series ($CFCl_2CH_2Cl$, $CF_2ClCH_2Cl$, $CCl_2=CHCl$, and the like) and especially of the 120 series ($CCl_3CHCl_2$, $CCl_2FCHCl_2$, $CF_2ClCHCl_2$, and the like). At low temperature, these chlorination reactions are only very slow, chlorine consumption is very low and very low amounts of chlorine are sufficient to maintain the activity of the fluorination catalyst. It is thus preferable to use between 0.05 and 0.5% of chlorine (molar % with respect to F142b).

The process according to the invention can be implemented batchwise but it is advantageously carried out continuously. In the latter case, the reaction can be carried out in conventional equipment well known to the person skilled in the art. It can be a reactor supplied, in the gaseous or liquid form, with the starting materials (F142 and HF) and the recycled materials and appropriately heated or cooled. It must promote contact between the reactants by an appropriate geometry, an appropriate method of introduction of the reactants and an appropriate mixing technique. The reactor can be surmounted by a column and by a retrograde condenser which makes it possible to prevent departure, in the gas flow exiting from the reactor, of the catalyst or catalysts used and to adjust the composition of organofluorinated compounds in this flow (content of F143a, F142b, and the like).

The starting materials or recyclates are supplied to the reactor in the ratio appropriate for production of F143a. This means, in the case of a complete recycling of the unconverted products, a fresh HF/fresh F142b molar ratio in the region of stoichiometry, that is to say in the region of 1. In practice, in order to take into account the HF removed with the F143a formed, the reactor is generally supplied with an HF/F142b mixture corresponding to an HF/F142b molar ratio slightly greater than 1, generally between 1.05 and 1.20.

As indicated above, the use of chlorine for maintaining the catalytic activity is reflected by the formation of chlorination products (essentially products of the 130, 120 and 110 series) or of other by-products which are heavy products in comparison with F143a and F142b and which therefor have a tendency to accumulate in the reactor. The concentration of heavy by-products not belonging to the 140 series in the reaction mixture is not critical but it has been found that the reaction is easier to carry out when this content is not excessively high. As a general rule, it is regulated so as to remain less than 75% by weight; the content of heavy by-products in the liquid reaction mixture can be adjusted by a purge of the reaction mixture.

The flows, gaseous and optionally liquid, resulting from the reaction are treated conventionally in order to separate the useful finished products therefrom (F143a, HCl). As regards the recovery of the hydrochloric acid, this treatment can in particular comprise a distillation of anhydrous HCl or washing the gas flow with water in order to separate the HCl and the organic products (essentially F143a). The F143a, the F142b, the other products of the 140 series (F141b, F140a) possibly formed, the unconverted hydrofluoric acid and the catalyst or catalysts used contained in the liquid purge of the reaction mixture can be recycled to the reaction system.

The following examples illustrate the invention without limiting it.

EXAMPLE 1

17 kg of F142b and 209 g of $SbCl_5$, i.e. 0.5% by weight of antimony with respect to the F142b, were introduced into a 30 litre conventional fluorination reactor, made of ordinary steel, surmounted by a retrograde column and a condenser. This mixture was then brought to reflux at 70° C. and the following were then introduced at this temperature:

4,800 g/h of F142b, i.e. 47.7 mol/h 1,020 g/h of HF, i.e. 51 mol/h 8.5 g/h of $Cl_2$, i.e. 0.25 mol % with respect to the F142b.

The pressure was gradually increased and, while maintaining the temperature at 70° C., it was allowed to rise to 17 bar absolute. The pressure was then regulated at this value of 17 bar by drawing off the gas flow at the outlet of the reflux condenser. Analysis of this gas flow, after washing with water in order to remove the HCl produced and the incompletely converted HF, allowed only a single organic impurity to be detected in the crude F143a: F142b, the content of which by weight was in the region of 2,000 ppm.

This test was continued for 500 hours, during which the operation of the reaction (temperature, pressure, outlet flow rate, analysis of the crude F143a, and the like) remained perfectly stable. After these 500 hours of operation, analysis of the reaction mixture made it possible to observe that this liquid contained approximately 30% by weight of heavy products outside the 140 series composed essentially of the following products:

| | |
|---|---|
| $CCl_3CCl_2H$ | F120 |
| $CFCl_2CCl_2H$ | F121 |
| $CFCl_2CH_2Cl$ | F131a |
| $CF_2ClCH_2Cl$ | F132b |
| $CCl_2=CHCl$ | F1120 |

EXAMPLE 2

17 kg of F142b and 209 g of $SbCl_5$ were introduced into the same reactor as that of Example 1. The mixture was then brought to reflux at 20° C. and the following were introduced at this temperature:

5,819 g/h of F142b, i.e. 57.9 mol/h 1,280 g/h of HF, i.e. 64 mol/h 20 g/h of $Cl_2$, i.e. 0.5 mol % with respect to the F142b.

The pressure was allowed to rise to 9 bar absolute, at which value it was regulated by drawing off the gas flow. After a starting-up period, the reaction temperature could be maintained between 15 and 20° C. and the operation of the reaction was perfectly stable. The crude F143a, obtained after washing the gaseous material drawn off downstream of the condenser with water, contained only a single detected impurity: F142b, at a content of 2 to 3% by weight.

The chlorine content of this gas flow was determined by analysis, after absorption in a sodium hydroxide/sodium sulphite solution. Analytical errors aside, the amount of chlorine found at the outlet corresponded to that introduced into the reactor. This very low reactivity of the chlorine at this temperature was confirmed by an analysis of the reaction mixture which, after 100 hours of operation, contained less than 1.5% of heavy products outside the 140 series.

After these 100 hours of operation, the temperature was gradually allowed to rise to 50° C. while maintaining the pressure at 9 bar. Analysis of the chlorine contained in the gaseous material drawn off made it possible to show that approximately 50% of the chlorine was consumed. This clearly demonstrates the influence of the temperature of the reaction mixture.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. A method of producing 1,1,1-trifluoroethane (F143a), comprising reacting in liquid phase, in the presence of a catalyst, 1-chloro-1,1,-difluoroethane (F142b) and anhydrous hydrofluoric acid, wherein the reacting is carried out continuously in the liquid phase in a reactor fed by F142b and hydrofluoric acid in a molar ratio of HF/F142b between 1.05 and 1.20.

2. The method according to claim 1, wherein the catalyst is a pentavalent antimony halide.

3. The method according to claim 2, wherein the pentavalent antimony halide is selected from antimony pentachloride and a pentavalent antimony chlorofluoride.

4. The method according to claim 2, wherein the weight content of antimony in the liquid reaction medium is between 0.01 and 10%.

5. The method according to claim 4, wherein the weight content of antimony in the liquid reaction medium is between 0.1 and 5%.

6. The method according to claim 1, wherein the reacting is carried out at an absolute pressure of between 5 and 30 bars.

7. The method according to claim 1, wherein the reacting is carried out at an absolute pressure of between 7 and 20 bars.

8. The method according to claim 1, wherein the reacting is carried out at a temperature between 0° and 120° C.

9. The method according to claim 1, wherein the reacting is carried out at a temperature between 10° and 85° C.

10. The method according to claim 1, wherein the reacting is carried out in the presence of chlorine, wherein the molar ratio of $Cl_2$/F142b is less than 0.025.

11. The method according to claim 1, wherein the reacting is carried out in the presence of chlorine, wherein the molar ratio of $Cl_2$/F142b is less than 0.01.

12. The method according to claim 1, wherein the reacting is carried out in the presence of chlorine, wherein the molar ratio of $Cl_2$/F142b is between 0.0005 and 0.005.

13. The method according to claim 1, wherein crude F143a obtained after washing a gaseous material drawn off downstream of a condenser with water contains from 97 to 99.8% by weight of F143a.

14. The method according to claim 1, wherein crude F143a obtained after washing a gaseous material drawn off downstream of a condenser with water contains, as an impurity, F142b at a content from 0.2% to 3% by weight.

15. The method according to claim 1, wherein crude F143a obtained after washing a gaseous material drawn off downstream of a condenser with water contains between 97 to 99.8% by weight of F143a, and wherein the crude F143a contains as an impurity, F142b at a content of 0.2% to 3% by weight.

* * * * *

UNITED STATES PATENT AND TRADEMARK OFFICE
CERTIFICATE OF CORRECTION

PATENT NO. : 6,339,178 B1 Page 1 of 1
DATED : January 15, 2002
INVENTOR(S) : Lantz et al.

It is certified that error appears in the above-identified patent and that said Letters Patent is hereby corrected as shown below:

<u>Title page,</u>
Item [*] Notice: delete the phrase "by 35 days" and insert -- by 36 days --

Signed and Sealed this

Eighteenth Day of May, 2004

JON W. DUDAS
*Acting Director of the United States Patent and Trademark Office*